US006204245B1

United States Patent
Siegel et al.

(10) Patent No.: US 6,204,245 B1
(45) Date of Patent: Mar. 20, 2001

(54) TREATMENT OF NARCOLEPSY WITH IMMUNOSUPPRESSANTS

(75) Inventors: Jerome M. Siegel; Lisa N. Boehmer, both of Northridge, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/398,260

(22) Filed: Sep. 17, 1999

(51) Int. Cl.$^7$ .................. A61K 38/00; A61K 31/675; A61K 31/67; A61K 31/60; A61K 31/56

(52) U.S. Cl. .................. 514/11; 514/90; 514/99; 514/165; 514/179; 514/180; 514/184; 514/249; 514/262; 514/291; 514/313; 514/404; 514/411; 514/420; 514/495; 514/562; 514/567; 514/569; 514/570; 514/649

(58) Field of Search .................. 514/11, 90, 99, 514/165, 179, 180, 184, 249, 262, 291, 313, 404, 411, 420, 495, 562, 567, 569, 570, 649

(56) References Cited

U.S. PATENT DOCUMENTS 3,980,665 * 9/1976 Fahnenstich et al. .
5,912,250 * 6/1999 Shintzky et al. .

OTHER PUBLICATIONS

Aldrich, M., "Narcolepsy and Related Disorders," *Sleep Medicine*, Chapter 10, pp. 152–174; Oxford University Press, New York, NY U.S.A. (1999).
Aldrich, M. S., "Narcolepsy," *New Eng. J. Med.*, 323389–394 (1990).
Aldrich, M. S., "Narcolepsy," *Neurology*, 42(Suppl. 6):34–43 (1992).
Aldrich, M. S., "The Neurobiology of Narcolepsy," *TINS*, 14(6):235–239 (1991).
Aldrich, M. S., "Diagnostic aspects of narcolepsy," *Neurology*, 50(suppl. 1):S2–S7, 1991.
Baker et al., "Canine narcolepsy–cataplexy syndrome: evidence for an inherited monoaminergic–cholinergic imbalance," *Brain Mechanisms of Sleep*, edited by McGinty et al.; New York: Raven Press, pp. 199–233 (1985).
Behar et al., "A New DRBI*12022 Allele (DRBI*12022) found in association with DQA1*0102 and DQB1*0602 in two black narcoleptic subjects," *Immunogenetics*, 41:52 (1995).
Billiard, M., "Narcolepsy, Clinical Features and Aetiology," *Ann. Clin. Res.*, 17:220–226 (1985).
Billiard et al., "Elevated antibodies to streptococcal antigens in narcoleptic subjects," *Sleep Res.*, 18:201, (1989), abstract only.
Broughton et al., "Psychosocial impact of narcolepsy," *Sleep*, 17:S45–S49 (1994).

Cadieux et al., "Pharmacologic and Psychotherapeutic Issues in Coexistent Paranoid Schizophrenia and Narcolepsy: Case Report," *J. Clin. Psychiatry.*, 46:191–193 (1985).
Cederberg et al., "Breeding history of the Stanford colony of narcoleptic dogs," *Vet. Rec.*, 142:31–36 (1998).
Chemelli et al., "Narcolepsy in *orexin* Knockout Mice: Molecular Genetics of Sleep Regulation," *Cell*, 98:437–451 (1999).
Delashaw et al., "Cholinergic Mechanisms and Cataplexy in Dogs," *Exp. Neurology*, 66:745–757 (1979).
Douglass et al., "Three Simultaneous Major Sleep Disorders," *Can. J. Psychiatry*, 32(1):57–60 (1987).
Douglas et al., "Florid Refractory Schgizophrenias That Turn Out to Be Treatable Variants of HLA–Associated Narcolepsy," *J. Nerv. Ment. Dis.*, 179(1):12–17 (1991).
Douglass et al., "Monozygotic twins concordant for the narcoleptic syndrome," *Neurology*, 39(1):140–141 (1989).
Erlich et al., "Narcolepsy: A Neuropathologic Study," *Sleep*, 9:126–132 (1986).
Foutz et al., "Genetic Factors in Canine Factors in Canine Narcolepsy," *Sleep*, 1(4):413–421 (1979).
Fredrickson et al., "CSF immune variables in patients with narcolepsy," *Acta. Neurol. Scan.*, 81:253–254 (1990).
Fry, J.M., "Treatment modalities for narcolepsy," *Neurology*, 50(Suppl 1): S43–S48 (1998).
Gaiser et al., "Evidence for an autoimmune etiology in canine narcolepsy," *Sleep Res.*, 18:230 (1989) abstract only.
Gibson et al., "HLA and Schizophrenia: Refutation of Reported Associations with A9 (A23/A24), DR4, and DQβ1*0602," *Am. J. Med. Genetics*, 88:416–421 (1999).
Green et al., "Narcolepsy Signs, Symptoms, Differential Diagnosis, and Management," *Arch. Fam. Med.*, 7:472–478 (1998).
GroBkopf et al., "Potential role for the narcolepsy–anmd multiple sclerosis–associated HLA allele DQB1*0602 in schizophrenia subtypes," *Schizophrenia Research*, 30:187–189 (1998).
Guilleminault et al., "Investigations into the neurologic basis of narcolepsy," *Neurology*, 50(Suppl. 1):S8–S15 edited by Fry, J.M. (1998).
Guilleminault, C., "Narcolepsy Syndrome", *Principles and Practice of Sleep Medicine, 2hu ndedition*, pp. 549–561, 1993.

(List continued on next page.)

Primary Examiner—William R. A. Jarvis
(74) *Attorney, Agent, or Firm*—Townsend and Townsend and Crew (57) ABSTRACT

The invention provides compositions and methods for treatment of narcolepsy or isolated cataplexy. Such methods entail administering a therapeutically effective regime of at least one immunosuppressive agent. The methods are particularly useful for prophylactic and therapeutic treatment of narcolepsy or isolated cataplexy.

33 Claims, 4 Drawing Sheets

OTHER PUBLICATIONS

Guilleminault et al., "Prazosin Contraindicated in Patients with Narcolepsy," *The Lancet,* 2(8609):511 (1988).

Hinze–Selch et al., "In vivo and in vitro immune variables in patients with narcolepsy and HLA–DR2 matched controls," *Neurology,* 50:1149–1152 (1998).

Honda et al., "Genetic Aspects of Narcolepsy," in *Handbook of Sleep Disorders,* edited by M. Thorpy; (Marcel Dekket, Inc., New York, NY) (1990), pp. 217–234.

Honda et al., "HLA–DR2 and Dw2 in narcolepsy and in other disorders of excessive somnolence without cataplexy," *Sleep,* 9(1):133–142 (1986).

Hublin et al., "The prevalence of narcolepsy: and epidemiological study of the Finnish twin cohort," *Ann. Neurol.,* 35(6):709–716 (1994).

Jacob et al., "Heritable major histocompatibility complex Class II–associated differences in production of tumor necrosis factor and relevance to genetic predisposition to systemic lupus erythematosus," *PNAS,* 87:1233–1237 (1990).

Kaitin et al., "Evidence for excessive sleepiness in canine narcoleptics," *Electroencheph. Clin. Neurophysiol.,* 64:447–454 (1986).

Kanbayashi et al., "Thalidomide, a hypnotic with immune modulating properties, increases cataplexy in canine narcolepsy," *Neuroreport,* 7(12):1881–1886 (1996).

Kilduff et al., "Immunosuppression with Cyclosporine as a Treatment for Canine Narcolepsy," *Sleep Research,* 16:369 (1987) abstract.

Klippel et al., *Rheumatology,* second edition, cover page and table of contents, London:Mosby (1998).

Krueger et al., "Cytokines in sleep regulation," *Sleep and sleep disorders: from molecule to behavior,* edited by Hayaishi and Inoue; pp. 261–277; Tokyo: Academic Press (1997).

Langdon et al., "Immune factors in narcolepsy," *Sleep,* 9(1):143–148 (1986).

Lin et al., "The Sleep Disorder Canine Narcolepsy Is Caused by a Mutation in the Hypocretin (Orexin) Receptor 2 Gene," *Cell,* 98:365–376 (1999).

Matsuki et al., "No male segregation distortion of DR2 Haplotypes in Japanese narcoleptic patients," *Human Immunology,* 23:23–26 (1988).

Matsuki et al., "HLA in Narcolepsy in Japan," chapter 3 from *HLA in Narcolepsy,* edited by Honda and Juji; pp. 58–76; New York: Springer Verlag (1988).

Matsuki et al., "DQ (rather than DR) genme marks susceptibility to narcolepsy," *Lancet,* 339:1052 (1992).

Mignot et al., "Genetic linkage of autosomal recessive canine narcolepsy with a $\mu$ immunoglobulin heavy–chain switch–like segment," *PNAS,* 88:3475–3478 (1991).

Mignot, E. et al., "DQBl*0602 and DQA1*0102 (DQ1) Are Better Markers Than Dr1 for Narcolepsy in Caucasian and Black Americans," *Sleep,* 17:S60–S67 (1994).

Mignot, E., "Genetic and familial aspects of narcolepsy," *Neurology,* 50(2)(Suppl 1):S16–S22 (1998).

Mignot et al., "Effect of $\alpha$1–adrenoceptors blockade with prazosin in canine narcolepsy," *Brain Res.,* 444:184–188 (1988).

Mignot, E. et al., "Narcolepsy and immunity," *Adv. Neuroimmunol.,* 5:23–37 (1995).

Mignot, E. et al., "Canine cataplexy is preferentiallyt controlled by adrenergic mechanisms: evidence using monoamine selective uptake inhibitors and release enhancers," *Psychopharmacology,* 113:76–82 (1993).

Mignot, E. et al., "Nocturnal Sleep and Daytime Sleepiness in normal Subjects with HLA–DQB1*0602," *Sleep,* 22(3):347–352 (1999).

Mitler, M. M. "Toward an animal model of narcolepsy–cataplexy," chapter 24 from *Narcolepsy,* edited by Guilleminault, Dement and Passouant; pp. 387–409; New York: Spectrum Publications, Inc. (1975).

Mitler et al., "Narcolepsy Diagnosis, Treatment, and Management," *Psych. Clin. N. Amer.,* 10(4):593–606 (1987).

Mitler, M. M. et al., "treatment of Narcolepsy with Methamphetamine," *Sleep,* 16(4):306–317 (1993).

Mitler, M. M., "Evaluation of Treatment Wioth Stimulants in Narcolepsy," *Sleep,* 17:S103–S106 (1994).

Montplaisir et al., "Streptococcal antibodies in narcolepsy and idiopathic hypersoimnia," *Sleep Res.,* 18:271 (1989) abstract only.

Motoyama et al., "Restriction fragment length polymorphism in canine narcolepsy," *Immunogenetics,* 29:124–126 (1989).

Mueller–Eckhardt et al., "Is there an infectious origin of narcolepsy?," *The Lancet,* 424 (1990).

Nishino, S. et al., "Desmethyl Metabolites of Serotonergic Uptake Inhibitors Are More Potent for Supressing Cannine Cataplexy Than Their Parent Compounds,"*Sleep,* 16:706–712 (1993).

Nishino, S. et al., "Pharmacological aspects of human and canine narcolepsy," *Prog. Neurobiol.,* 52:27–78 (1997).

Opp et al., "Interleukin–10 (cytokine synthesis inhibitory factopr) acts in the central nervous system of rats to reduce sleep,"*J. Neuroimmunol.,* 60:165–168 (1995).

Pollmacher et al., "DR–2 Positive monizygotic twins discordant for narcoepsy," *Sleep,* 13(4):336–343 (1990).

Robinson et al., "Narcolepsy," chapter 25 from *Sleep Disorders Medicine: Basic Science, Technical Considerations, and Clinical Aspects,* edited by Chokroverty, S.; Butterworth Heinemann Boston, MA U.S.A.(1999) pp. 427–440.

Rubin et al., "HLA–DR2 association with excessive somnolence in narcolepsy does not generalize to sleep apnea and is not accomplanied by systemic autoimmune abnormalities," *Clin. Immunol. Immunbopathol.,* 49:149–158 (1988).

Siegel, J.M. et al., "Neuronal degeneration in canine narcolepsy," *J. Neuroscience,* 19(1):248–257 (1999).

Sinha et al., "Autoimmune Diseases: The Failure of Self Tolerance," *Science,* 248:1380–1388 (1990).

Stein et al., "Glucocorticoids," chapter 50 from *Texbook of Rheumatology,* edited by Kelly et al.; pp. 787–803 (1997).

Tafti et al., "Major histocompatibility Class II molecules in the CNS: increased microglial expression at the onset of narcolepsy in canine model.," *J. Neurosci.,* 16(15):4588–4595 (1996).

Vgnotzas, A. N. et al., "Sleep and It's Disorders," *Annu. Rev. Med.,* 50:387–400 (1999).

Yoss et al., "Narcolepsy in children," *Pediatrics,* 25:1025–1033 (1960).

* cited by examiner

TREATMENT OF NARCOLEPSY WITH IMMUNOSUPPRESSANTS

STATEMENT AS TO RIGHTS TO INVENTIONS MADE UNDER FEDERALLY SPONSORED RESEARCH AND DEVELOPMENT

This invention was made with Government support under Grant No. NS14610, awarded by the National Institutes of Health; and the Veterans Administration. The Government has certain rights in this invention.

TECHNICAL FIELD

This invention resides in the fields of neurology, immunology, and medicine and relates to the treatment of narcolepsy, and immunosuppressive agents and compositions useful therein.

BACKGROUND OF THE INVENTION

Narcolepsy is a disabling neurological disorder that was first recognized 118 years ago by Gélineau, J. B. (De la narcolepsie, Gazette des Hopitaux Paris (1880) 53: 626–628). For a review of narcolepsy, see generally Chokroverty, S. (ed.), *Sleep Disorders Medicine: Basic Science, Technical Considerations, and Clinical Aspects*, $2_2$nd edition, Butterworth Heinemann, Boston, Mass. U.S.A. 1999; Aldrich, M., *Sleep Medicine*, Oxford University Press, New York, N.Y. U.S.A. 1999; Vgnotzas, A. N. et al., *Annu. Rev. Med.* (1999) 50:387–400; and Guillenminault, C., *Narcolepsy Syndrome* in *Principles and Practice of Sleep Medicine*, $2^{nd}$ edition (Kryger, M. H., et al. (eds.), (W. B. Saunders Philadelphia, Pa. U.S.A. 1989), pages 338–246). The symptoms of narcolepsy include excessive daytime sleepiness (EDS), hypnagogic and hypnopompic hallucinations (hallucinations during transitions into and out of sleep, respectively), cataplexy (sudden and reversible loss of muscle tone), sleep paralysis (an inability to move at sleep onset or awakening) and REM sleep at sleep onset (Guilleminault, C. 1989). In narcoleptics, sleep occurs at inappropriate times and in dangerous and embarrassing situations. Although total sleep time is near normal, nighttime sleep is disrupted by frequent awakenings (Mitler, M. et al., *Psych Clin. N. Amer.* (1987) 10:593–606). Cataplexy, a temporary, partial or complete paralysis due to a sudden loss of muscle tone, with unimpaired consciousness, is typically triggered by sudden strong emotions, such as those accompanying laughter, anger and embarrassment. In some patients, status cataplecticus, or periods of repetitive loss of muscle tone, occurs and can last for hours or days.

Narcolepsy has also been reported to occur in other animals and has been most intensively studied in canines (Foutz, A. S., et al., (1979) Sleep 1:413–421; Nishino, S. and Mignot, E. (1997) *Prog. Neurobiol.* 52:27–78; Cederberg, R., et al., (1998) *Vet. Rec.* 142, 31–36). Canine narcolepsy in Doberman pinschers and Labrador Retrievers is transmitted as an apparently single gene autosomal recessive trait with full penetrance, canarc-1 (Foutz, A. S., et al., (1979) *Sleep* 1:413–421; Baker, T.L. and Dement, W. C. (1985), Canine narcolepsy-cataplexy syndrome: evidence for an inherited monoaminergic-cholinergic imbalance in *Brain Mechanisms of Sleep*, D. J. McGinty, R. Drucker-Colin, A. Morrison, and P. L. Parmeggiani, eds. (New York: Raven Press), pages 199–233). A large number of physiological and pharmacological studies have demonstrated a close similarity between human and canine narcolepsy (Baker, T. L. and Dement, W. C. (1985) and Nishino, S. and Mignot, E. (1997)). These animals have all the major symptoms defining narcolepsy in humans, including episodes of cataplexy. Canine narcoleptics also exhibit excessive daytime sleepiness and interrupted sleep periods (Kaitin, K. I. et al., *Electroenceph. Clin. Neurophysiol.* (1986) 64:447–454). Cholinergic antagonists block cataplexy in both canine and human narcoleptics (Delashaw et al., (1979) *Exp. Neurology* 66:745–757). α1 blockers (such as prazosin) exacerbate cataplexy in dogs and humans and can produce *status cataplecticus* in both species (Mignot et al., (1988) *Brain Res.* 444:184–188; Guilleminault et al., (1988) *The Lancet* 2: 511). Drugs used to treat cataplexy and excessive sleepiness in humans are also effective in narcoleptics dogs (Baker and Dement, 1985). Narcolepsy usually does not develop until adolescence in humans, but it can be seen as early as three or as late as 45 years of age or older (Yoss and Daly, (1960) *Pediatrics* 25:1025–1033; Billiard, (1985) *Ann. Clin.Res* 17:220–226). The appearance of cataplexy, as a proxy variable for the onset of narcolepsy/cataplexy, in canine narcolepsy, develops between 4 and 24 weeks of age.

Approximately 250,000 Americans have narcolepsy (Aldrich, M. S., *New Eng. J. Med.* (1990) 323:389–394). Although familial cases of narcolepsy have been reported, most human occurrences are sporadic, and the disorder is generally believed to be multigenic and environmentally influenced (Honda, Y., and Matsuki, K., *Genetic Aspects of Narcolepsy* in *Handbook of Sleep Disorders*, M. Thorpy (ed.) (Marcel Dekker, Inc., New York, N.Y. 1990), pages 217–234). One predisposing genetic factor is a specific HLA-DQ allele, HLA-DQB1*0602 (Matsuki, K., et al., (1992) *Lancet* 339:1052. Mignot, E., et al., (1994) *Sleep* 17:S60–S67; Mignot, E. (1998) *Neurology* 50:S16–S22). Approximately 95% of narcoleptics have this HLA haplotype, compared to only 30% of the general population (Aldrich, M. S., *New Eng. J Med.* (1990) 323:389–394). An autoimmune mechanism has been reported in some HLA-associated diseases such as juvenile diabetes, celiac disease, systemic lupus erythematosus and rheumatoid arthritis (Sinha, A. et al., *Science* (1990) 248:1380–1388); however, all attempts to date to test the autoimmune hypothesis for narcolepsy have failed (Mignot, E., et al., *Adv. Neuroimmunol.* (1995) 5:23–37).

It has recently been reported that narcolepsy is linked to dysfunction of the newly discovered hypocretin (Hcrt) (orexin) peptide system. This report was based on a deletion in the transcripts of the hypocretin receptor 2 (Hcrtr2) gene in narcoleptic Dobermans and Labradors (Lin, L. et. al., *Cell* (1999) 97:365–376). Chemelli et al. created Hcrt knockout mice which have abnormalities of sleep control resembling aspects of narcolepsy (Chemelli, R. M. et al., *Cell* (1999) 98:437–451), as well.

Narcolepsy requires long-term management of symptoms (Fry, J., *Neurology* (1998) 50(2 Suppl 1):S8–15). Interventions can be nonpharmacologic, such as lifestyle changes, and pharmacologic, for relief of daytime sleepiness, cataplexy, sleep paralysis, hypnagogic hallucinations, and/or hypnopompic hallucinations. Pharmacologic treatment of narcolepsy has depended on the use of central nervous system (CNS) stimulants to increase wakefulness or to reduce the number and severity of cataplectic attacks or hypnagogic hallucinations. CNS stimulants can be effective in relieving the sleepiness of narcolepsy; however, extremely high doses are necessary to restore alertness to normal levels (Mitler, M. et al., *Sleep* (1993) 16:306–317). Such doses can have very dangerous side effects. Because of these side effects, most narcoleptics use stimulants only when absolutely needed or continuously use low-level doses not capable of restoring normal levels of alertness. Periodic "drug holidays" can sometimes be employed to maintain the effectiveness of stimulants (Mitler, M. S. *Sleep* (1994) 17:S103–S106). Frequent naps can be effective in permitting periods of waking alertness (Aldrich, M. S., *Neurology* (1992) 42(S6):34–43). Cataplexy can sometimes be treated successfully with tricyclic antidepressants or selective serotonin reuptake inhibitors (SSRI's), among other medications. Both tricyclic antidepressant drugs and SSRI's all appear to act by producing metabolites that activate noradrenergic receptors (Nishino, S. et al., *Sleep* (1993) 16:706–712; Mignot, E. et al., *Psychopharmacology* (1993) 113:76–82). Even with these treatments, accidents due to sleepiness and cataplexy are common and professional and educational attainment are significantly reduced in narcoleptics (Broughton, W. A. and Broughton, R. J., *Sleep* (1994) 17:S45–S49).

SUMMARY OF THE INVENTION

In one aspect, the invention provides methods of treating narcolepsy or isolated cataplexy in a patient. Such methods entail administering to a patient susceptible to or suffering from narcolepsy or isolated cataplexy a therapeutically effective regime of at least one immunosuppressive agent. In some methods, the immunosuppressive agent prevents or reduces the occurrence of one or more symptoms associated with narcolepsy or isolated cataplexy in the patient. These symptoms can include abnormal sleep features, overwhelming episodes of sleep, excessive daytime somnolence, abnormal REM sleep, hypnagogic and hypnopompic hallucinations, disturbed nocturnal sleep, cataplexy, and sleep paralysis. In some methods, the immunosuppressive agent is administered before onset of symptoms of narcolepsy or isolated cataplexy in a patient. In some methods, the immunosuppressive agent inhibits T cell, B cell, or monocyte infiltration associated with narcolepsy in the patient. In some methods, the patient has inherited risk factors indicating susceptibility to narcolepsy. Such risk factors include the presence of the genetic marker HLA-DQB1*0602, a mutation or deletion in any Hypocretin (Orexin) Receptor gene, or a mutation or deletion in the Hypocretin (Orexin) gene. In other methods, the patient has no known risk factors for narcolepsy. In some methods, the patient can show HLA-DQB1*0602-linked sleepiness and the therapeutically effective regime inhibits, arrests or reverses the HLA-DQB1*0602-linked sleepiness. In other methods, the patient can show neurodegeneration and the therapeutically effective regime inhibits, arrests or reverses the neurodegeneration.

For treatment of patients susceptible to or suffering from narcolepsy or isolated cataplexy, one treatment regime entails administering at least one immunosuppressive agent selected from the group consisting of a nonsteroidal anti-inflammatory drug, a glucocorticoid, hydroxychloroquine, sulfaxalazine, methotrexate, aurothioglucose, aurothiomalate, auronofin, D-penicillamine, azathioprine, cyclophosphamide, cyclosporin A, FK506, and rapamycin. Another treatment regime entails the administration of at least two of these immunsuppressive agents. A further treatment regime entails administering an immunosuppressive agent in combination with at least one agent selected from the group consisting of a tricyclic antidepressant, a tetracyclic antidepressant, a selective serotonin reuptake inhibitor (SSRI), a monoamine oxidase (MAO) inhibitor, caffeine, theophiline, theobromine, amphetamine, methylphenidate, dextroamphetamine, methamphetamine, pemoline, mazindol, modafinil, selegiline, ritanserin, viloxazine, CRL 40476, clomipramine, protriptyline, imipramine, desipramine, fluoxetine, paroxitine, sertraline, gammahydroxybutyrate (GHB), clonazepam, carbamazepine, and yohimbine. In some methods, the glucocorticoid is dexamethasone, methylprednisolone, prednisolone, or prednisone. In some such methods, the glucocorticoid compound is administered in combination with a therapeutically effective amount of a nonsteroidal anti-inflammatory agent. In some such methods, the nonsteroidal anti-inflammatory agent is an aspirin compound (acetylsalicylate), a non-aspirin salicylate, diclofenac, diflunisal, etodolac, fenoprofen, flurbiprofen, ibuprofen, indomethacin, ketoprofen, meclofenamate, naproxen, naproxen sodium, phenylbutazone, sulindac, or tometin. In some methods, the glucocorticoid compound is administered in combination with a therapeutically effective amount of an agent selected from the group consisting of hydroxychloroquine, sulfaxalazine, methotrexate, aurothioglucose, aurothiomalate, auronofin, D-penicillamine, azathioprine, cyclophosphamide, cyclosporin A, FK506, and rapamycin. In some methods the therapeutic agent is selected from the group consisting of:an anti-inflammatory cytokine, an anti-TNF-V antibody, a COX-1 inhibitor, a COX-2 inhibitor, an iNOS inhibitor, an nNOS inhibitor, and an antioxidant.

The immunosuppressive agent is typically administered by intravenous infusion, transdermal delivery, intramuscular delivery, subcutaneous delivery, intracerebralventricular delivery, oral delivery, or by inhalation. Typically, the patient is monitored following administration to assess the effects of treatment. Some such monitoring includes conducting a nocturnal polysomnogram (PSG), Multiple Sleep Latency Test (MSLT), Epworth Sleepiness Scale (EPS) questionnaire, Maintenance of Wakefulness Test (MWT), pupilography, electroencephalograms, electroencephalographic spectral analysis, actigraphy, or maintaining a log of incidence of cataplexy including their number, severity and duration. Other methods of monitoring include conducting immune or histological assays to determine the presence or absence of neurodegeneration, nerve cell death, T cell infiltration, B cell infiltration, monocytic infiltration, apoptosis, or necrosis.

In some methods, the therapeutically effective regime can be administered from birth of the patient to prevent or delay onset of narcolepsy or isolated cataplexy in the patient. In other methods, the therapeutically effective regime can be administered after diagnosis of a symptom of narcolepsy in the patient to relieve the symptom, or arrest or inhibit further development of the symptom.

In another aspect, the invention provides pharmaceutical compositions bearing labels indicating suitability for treating narcolepsy or isolated cataplexy comprising at least one immunosuppressive agent effective to suppress the symptoms associated with narcolepsy or isolated cataplexy administered together with a pharmaceutically acceptable carrier. Some compositions can further comprise a nonsteroidal anti-inflammatory, a glucocorticoid, hydroxychloroquine, sulfaxalazine, methotrexate, aurothioglucose, aurothiomalate, auronofin, D-penicillamine, azathioprine, cyclophosphamide, cyclosporin A, FK506, or rapamycin.

The invention further provides methods of treating schizophrenia in a patient. Such methods entail administering to a patient susceptible to or suffering from schizophrenia a therapeutically effective regime of one or more immunosuppressive agents. In some methods, the patient has inherited risk factors indicating susceptibility to schizophrenia. Such risk factors can include the presence of the genetic marker HLA-DQB1*0602.

BRIEF DESCRIPTION OF THE DRAWINGS

FIGS. 2(A–D). Actigraph data showing sleep normalization as a result of the action of immunosuppressive regime in a narcoleptic canine.

FIG. 3. A. Three day immunosuppression treatment with glucocorticoids, azathioprine and methotrexate in a three month old narcoleptic canine. B. Two week long immunosuppression treatment with methylprednisone alone in the same canine treated in (A) at eight months of age. This figure shows that the immunosuppressive agents themselves do not reduce symptoms, but rather that they exert their effect by preventing symptom development.

FIG. 4(A and B). CD3+ T cell infiltration in the amygdala of a one month old untreated narcoleptic canine.

DETAILED DESCRIPTION

Definitions

The term patient includes mammals, such as humans, domestic animals (e.g., dogs or cats), farm animals (cattle, horses, or pigs), monkeys, rabbits, rats, mice, and other laboratory animals.

The term autoimmune disease refers to a spontaneous or induced malfunction of the immune system of mammals in which the immune system fails to distinguish between foreign immunogenic substances within the mammal and/or autologous ("self") substances and, as a result, treats autologous ("self") tissues and substances as if they were foreign and mounts an immune response against them. Autoimmune disease is characterized by production of either antibodies that react with self tissue, and/or the activation of immune effector T cells that are autoreactive to endogenous self antigens. Three main immunopathologic mechanisms act to mediate autoimmune diseases: 1) autoantibodies are directed against functional cellular receptors or other cell surface molecules, and either stimulate or inhibit specialized cellular function with or without destruction of cells or tissues; 2) autoantigen—autoantibody immune complexes form in intercellular fluids or in the general circulation and ultimately mediate tissue damage; and 3) lymphocytes produce tissue lesions by release of cytokines or by attracting other destructive inflammatory cell types to the lesions. These inflammatory cells in turn lead to production of lipid mediators and cytokines with associated inflammatory disease.

The term inflammation refers to both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

The term immune-mediated refers to a process that is either autoimmune or inflammatory in nature.

The term major histocompatibility complex (MHC) refers to a plurality of cell surface proteins and glycoproteins that are present on the surfaces of mammalian cells and which mediate cell-cell interactions (e.g. tissue compatibility in organ and tissue transplantation) and the immune response in a mammal. The MHC is encoded in humans by the HLA complex, in dogs by the DLA complex and in mice by the H-2 complex. The primary immunological function of MHC molecules is to bind and "present" pieces of antigenic molecules on the surfaces of cells for recognition (binding) by the antigen-specific T cell receptors (TCRs) of lymphocytes. Differential structural properties of MHC class I and class II molecules account for their respective roles in activating different populations of T lymphocytes (T cells). MHC class I molecules specifically bind CD8 molecules expressed on cytotoxic T lymphocytes (Tc cells). MHC class II molecules specifically bind CD4 molecules expressed on helper T lymphocytes ($T_H$ cells). MHC class I expression is widespread on virtually every cell of the body. This is consistent with the protective function of $T_C$ cells which continuously survey cell surfaces and kill cells harboring metabolically active microorganisms infecting these cells. MHC class II expression is restricted to "antigen presenting cells" (or APCs). This is consistent with the functions of TH cells which are locally activated wherever these cells encounter macrophages, dendritic cells, follicular dendritic cells or B lymphocytes (B cells) that have internalized and processed antigens produced by pathogenic organisms and display pieces of these antigens using MHC class II molecules.

The term antibody is used to include intact antibodies and binding fragments thereof. Typically, fragments compete with the intact antibody from which they were derived and with other antibodies for specific binding to an antigen.

The term molecule is used broadly to mean an organic or inorganic chemical such as a drug; a peptide, including a variant or modified peptide or peptide-like substance such as a peptidomimetic or peptoid; or a protein such as an antibody or a growth factor receptor or a fragment thereof, such as an $F_v$, $F_c$ or $F_{ab}$ fragment of an antibody, which contains a binding domain. A molecule can be nonnaturally occurring, produced as a result of in vitro methods, or can be naturally occurring, such as a protein or fragment thereof expressed from a cDNA library.

The term specific binding (and equivalent phrases) refers to the ability of a binding moiety (e.g., a receptor, antibody, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ $M^{-1}$, and preferably at least about $10^7$, $10^8$, $10^9$, or $10^{10}$ $M^{-1}$. In some embodiments specific (or selective) binding is assayed (and specific binding molecules identified) according to the method of U.S. Pat. No. 5,622,699; this reference and all references cited therein are incorporated herein by reference. Typically a specific or selective reaction according to this assay is at least about twice background signal or noise and more typically at least about 5 or at least about 100 times background, or more.

When the binding moiety is an antibody, a variety of immunoassay formats can be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual,* Cold Spring Harbor Publications, New York, for a description of immunoassay formats and conditions that can be used to determine specific immunoreactivity (this reference and references cited therein are incorporated herein by reference).

(1) General

The invention is premised, in part, on the result that administration of an immunosuppressive agent to canines with a hereditary form of narcolepsy prevents and/or reduces development of symptoms of narcolepsy. This and other results described in the Examples section lead to the conclusion that existing immunosuppressive agents can be used for treatment of narcolepsy in humans and other mammals. The invention provides therapeutically effective regimes for administering immunosuppressive agents to subjects having or susceptible to narcolepsy. The agents used in such regimes can be standard immunosuppressants such as cyclosporin A, prednisone, azathioprine or methotrexate used in treatment of other diseases of the immune system, such as rheumatoid arthritis and graft vs. host disease. Furthermore, the treatment regimes can employ similar dosages, routes of administration and frequency of administration to those used in treating other immune-mediated disorders. Although practice of the present methods is not dependent on an understanding of mechanism, the results provided by the application suggest that narcolepsy is, at least in part, an immune-mediated disease, and that immunosuppressive agents provide effective treatment by preventing or inhibiting immune responses that would otherwise effect immune-mediated neurodegeneration.

(2) Narcolepsy

Narcolepsy is a chronic neurological disorder characterized by recurring episodes of sleep or sleepiness during the day, and often disrupted nocturnal REM sleep (see, e.g., Chokroverty, S. (ed.), *Sleep Disorders Medicine: Basic Science, Technical Considerations, and Clinical Aspects,* 2$^{nd}$ edition, Butterworth Heinemann, Boston, Mass. U.S.A. 1999; Aldrich, M., *Sleep Medicine,* Oxford University Press, New York, N.Y. U.S.A. 1999; these references and all references cited therein are herein incorporated by reference). Symptoms of narcolepsy include abnormal sleep features, overwhelming episodes of sleep, excessive daytime somnolence (EDS), abnormal REM sleep, hypnagogic and hypnopompic hallucinations, disturbed nocturnal sleep, cataplexy, and sleep paralysis. EDS includes daytime sleep attacks, which may occur with or without warning; persistent drowsiness, which may continue for prolonged periods of time; and "microsleeps" or fleeting moments of sleep intruding into the waking state. Cataplexy is usually an abrupt and reversible decrease or loss of muscle tone most frequently elicited by emotion. It can involve a limited number of muscles or the entire voluntary musculature except the extraocular muscles and to some extent the diaphragm. Typically, the jaw sags, the head falls forward, the arms drop to the side, and/or the knees unlock, or the cataplectic human may fall completely on the ground. The duration of a cataplectic attack, partial or total, usually varies from a few seconds to thirty minutes. Attacks can be elicited by emotion, stress, fatigue, exercise or heavy meals. Sleep paralysis is an experience that occurs when an individual falls asleep or awakens, and is very akin to complete cataplectic episodes. Patients can find themselves suddenly unable to move, speak, open their eyes, or even breathe deeply. Hypnagogic hallucinations often involve vision, and the manifestations usually consist of simple forms (i.e., colored circles, parts of objects) that may be constant in size or changing, or may be quite complex in their scenario. Auditory hallucinations are also common and can range from a collection of sounds to an elaborate speech or melody. Hallucinations at sleep onset can involve elementary cenesthopathic (abnormal) sensations (e.g., prickling, rubbing, light touching), changes in location of body parts, or feelings of levitation or extracorporeal experiences. Patients having cataplexy without EDS are said to have isolated cataplexy. Other symptoms of narcolepsy besides EDS may or may not be present in such patients. Narcolepsy and isolated cataplexy are classified as separate indications by FDA. Nevertheless, this classification does not imply a separate basis. Both indications can be treated by the methods described in the application.

(3) Patients Amenable to Treatment

Patients amenable to treatment include patients who are presently asymptomatic but who are at risk of developing symptomatic narcolepsy or isolated cataplexy at a later time. Such individuals include those having relatives who have experienced this disease, and those whose risk is determined by analysis of genetic or biochemical markers, or by biochemical methods. Other patients who are amenable to treatment include individuals free of diseases, other than narcolepsy or isolated cataplexy, that require immunosuppressive treatment. Additional patients amenable to treatment can include patients wherein the administration of the treatment ameliorates, prevents, or reduces one or more symptoms of narcolepsy or isolated cataplexy within six months of treatment. Patients to receive treatment can also include individuals who are not diagnosed with any disease of the immune system, or who are not diagnosed with any disease requiring immunosuppressive treatment.

Genetic markers of risk of developing narcolepsy include the presence of the HLA allele, HLADQB1*0602. The HLA-DQB1*0602 allele has also been linked to subclinical abnormal nocturnal REM sleep and increased daytime sleepiness in normal subjects as well as certain schizophrenia subtypes (see, e.g., Mignot, E., et al., *Sleep* (1999) 22(3):347–352; Cadieux, R., et al., *J. Clin. Psychol.* (1985) 46:191–193; Douglass, A., et al., *J. Nerv. Ment. Dis.* (1991) 179:12–17; these references and all references cited therein are herein incorporated by reference). The presence or absence of HLA-DQB1*0602 can be determined by standard procedures (see, e.g., Mignot, E., et al., *Sleep* (1999) 22(3):347–352, U.S. Pat. Nos. 5,908,749, 5,565,548, 5,541, 065, 5,196,308; these references are herein incorporated by reference). Other markers include a mutation or deletion in any Hypocretin (Orexin) Receptor gene, the prepro-Hypocretin (Orexin) gene itself, or in the Hypocretin (Orexin) Receptor 1 or Hypocretin (Orexin) Receptor 2 gene. Additional risk factors for narcolepsy and/or cataplexy include having Niemann-Pick disease type C or Norrie's disease.

Biochemical markers of risk include a defect in the proteolytic processing of the prepro-orexin precursor of the known hypocretin (orexin) molecules, or in the posttranslational modification mechanism that results in the normal production of Hcrt1 (orexin-A) and Hcrt2 (orexin-B) molecules. Other biochemical markers of risk for narcolepsy include autoantibodies or activated lymphocytes in the blood in individuals free of other immune-mediated and/or neoplastic diseases, or the presence of specific autoantibodies in individuals with or without other immune-mediated and/or neoplastic diseases. The presence of such markers in asymptomatic individuals signifies that the immune-mediated process leading to narcolepsy or cataplexy is almost certainly underway, although has not yet progressed so far as to produce symptoms.

In asymptomatic individuals, treatment can begin at any age including antenatally, or at birth. Usually, treatment is begun before a individual is 45 years old because if an individual has not developed narcolepsy or isolated cataplexy by that time, he or she probably will not do so at all. If a biochemical marker of disease, such as an autoantibody or activated T cell is detected, treatment should usually begin shortly thereafter. If likelihood of developing narcolepsy or isolated cataplexy is based on relatives having the disease or detection of a genetic marker, treatment can also be administered shortly after identification of these risk factors, or shortly after diagnosis. Alternatively, an individual found to possess a genetic marker can be left untreated but subjected to regular monitoring for biochemical or symptomatic changes without treatment. The decision whether to treat immediately or to monitor symptoms depends in part on the extent of risk predicted by the genetic marker(s) found in the individual. Once begun, immunosuppressive treatment is typically continued at intervals for a period of a week, a month, three months, six months or a year. In some patients, treatment is administered for up to the rest of a patient's life. Treatment can generally be stopped if a biochemical risk marker disappears. Treatment can sometimes be temporarily discontinued if the subject is infected with a pathogen for which a full immune response is needed for clearance. In veterinary patients, such as dogs having a hereditary form of narcolepsy, treatment is usually begun at anytime between birth to five months of age.

Other individuals amenable to treatment show or have shown behavioral symptoms of narcolepsy (i.e., symptomatic patients). Such symptoms can be detected by any of the techniques described below. In addition, symptomatic patients often have biochemical or genetic risk factors as described for asymptomatic individuals. In symptomatic patients, treatment usually begins at or shortly after diagnosis of symptoms. Treatment is typically continued at intervals for a week, a month, six months, a year or up to the rest of the patient's life. Typically, the patient's symptoms are monitored. If monitoring indicates a sustained reduction or elimination of symptoms for a period of at least a month, and preferably at least three months, treatment can be terminated or reduced in dosage. Monitoring is continued and treatment is resumed if symptoms reappear or worsen. If treatment causes no significant amelioration of symptoms in a patient for a period of at least six months, and typically at least one year, indicating that irreversible brain damage has occurred, or if the side effects of the treatment are intolerable to a patient, then treatment can be discontinued.

(4) Diagnostic and Monitoring Methods

Overt symptoms of narcolepsy can be detected as described by, e.g., Chokroverty, S. (ed.), *Sleep Disorders Medicine: Basic Science, Technical Considerations, and Clinical Aspects*, 2$^{nd}$ edition, Butterworth Heinemann, Boston, Mass. U.S.A. 1999; Aldrich, M., *Sleep Medicine*, Oxford University Press, New York, N.Y. U.S.A. 1999; these references and all references cited therein are herein incorporated by reference. The monitoring can include conducting a nocturnal polysomnogram (PSG), Multiple Sleep Latency Test (MSLT), Epworth Sleepiness Scale (EPS) questionnaire, Maintenance of Wakefulness Test (MWT), pupilography, electroencephalograms, electroencephalographic spectral analysis, actigraphy, or maintaining a log of incidence of cataplexy including their number, severity and duration.

Biochemical symptoms of narcolepsy, in the periphery or CNS, such as autoantibodies and/or activated peripheral lymphocytes recognizing an autoantigen, and/or oligoclonal bands, can be detected by conventional immunological assays. Genetic mutations associated with risk of narcolepsy can be detected by a variety of assays including allele specific hybridization and DNA sequencing, in addition to clinical diagnoses.

(5) Treatment Agents

The treatment agents of the present invention include immunosuppressive agents. Immunosuppressive agents are agents capable of suppressing immune responses. These agents include cytotoxic drugs, corticosteriods, nonsteroidal anti-inflammatory drugs (NSAIDs), specific T-lymphocyte immunosuppressants, and antibodies or fragments thereof (see *Physicians' Desk Reference*, 53$^{rd}$ edition, Medical Economics Company Inc., Montvale, N.J. (1999); this reference and all references cited therein are herein incorporated by reference).

Cytotoxic or antimetabolic drugs include hydroxychloroquine, sulfaxalazine, methotrexate, aurothioglucose, aurothiomalate, auronofin, D-penicillamine, azathioprine, and cyclophosphamide.

Glucocorticoids include dexamethasone, methylprednisolone, prednisolone, and prednisone.

NSAIDs include aspirin compounds (acetylsalicylates), non-aspirin salicylates, diclofenac, diflunisal, etodolac, fenoprofen, flurbiprofen, ibuprofen, indomethacin, ketoprofen, meclofenamate, naproxen, naproxen sodium, phenylbutazone, sulindac, and tometin.

Specific T-lymphocyte inununosuppressants include cyclosporin A, FK506, and rapamycin.

Treatment agents also can include other agents such as tricyclic antidepressants, tetracyclic antidepressants, SSRIs, monoamine oxidase (MAO) inhibitors, caffeine, theophiline, theobromine, amphetamine, methylphenidate, dextroamphetamine, methamphetamine, pemoline, mazindol, modafinil, selegiline, ritanserin, viloxazine, CRL 40476, clomipramine, protriptyline, imipramine, desipramine, fluoxetine, paroxitine, sertraline, gammahydroxybutyrate (GHB), clonazepam, carbamazepine, and yohimbine.

Other treatment agents include anti-inflammatory cytokines, anti-TNF-∀ antibodies, COX-1 inhibitors, COX-2 inhibitors, iNOS inhibitors, nNOS inhibitors, and antioxidants.

(6) Treatment Regimes

In prophylactic application, pharmaceutical compositions or medicants are administered to a patient susceptible to, or otherwise at risk for developing narcolepsy in an amount sufficient to prevent, reduce, or arrest the development of narcoleptic symptoms. In therapeutic applications, compositions or medicants are administered to a patient suspected to develop, or already suffering from narcolepsy and/or cataplexy in an amount sufficient to reverse, arrest, or at least partially arrest, the symptoms of narcolepsy and/or cataplexy. In both prophylactic and therapeutic regimes, immunosuppressive agents and other compounds of the invention are usually administered in several dosages until a sufficient response has been achieved. Typically, the treatment is monitored and repeated dosages can be given.

The amount of immunosuppressive agents and other active agents that can be combined with a carrier material to produce a single dosage form vary depending upon the disease treated, the type of drug, the mammalian species, and the particular mode of administration. Unit doses of the immunosuppressive agents and other compounds of the invention are usually within the Physicians' Desk Reference (PDR) specified maximum ranges and treatment regimens as well as the U.S. Federal Drug Agency-approved guidelines (see, *Physicians' Desk Reference*, 53$^{rd}$ edition, (1999) Medical Economics Company Inc., Montvale, N.J.). As a general guide, suitable unit doses for the immunosuppressive agents and other compounds of the present invention, for example, can contain between 0.1 mg/kg/week to about 10 mg/kg/week of the active compound. An exemplary unit dose is between 7.5 mg to about 190 mg. An alternative unit dose, corresponds to between 0.2 mg/kg to about 0.4 mg/kg, depending on the individual. Such unit doses can be administered more than once a day, for example 1, 2, 3, 4, 5 or 6 times a day, so that the total daily dosage for a 70 kg adult is in the range of about 12.5 mg to about 18.5 mg. Another exemplary dosage is 0.1 to about 0.25 mg/kg/week, and such therapy can extend for a number of weeks or months, and in some cases, years. A typical dosage can be a 10–1500 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

Suggested dosages for two specific immunosuppressive agents are as follows: prednisone can be given orally in doses between 0.1 to 2 mg/kg/day, although doses of 2 mg/kg/day would ordinarily not be given on a long term basis. In addition, prednisone can be given on alternate days. Azathioprine can be given orally once or twice a day in dosages from 0.1 to 4 mg/kg/day although dosages of 0.5 to 2.5 mg/kg/day would be more usual.

The specific dose level for any particular patient can depend on a variety of factors including the activity of the specific compound employed; the age, body weight, general health, sex and diet of the individual being treated; the time and route of administration; the rate of metabolism or excretion; other drugs which are concurrently or have previously been administered; and the severity of the particular disease undergoing therapy.

In some instances, dosages outside the above ranges are used to interrupt, adjust, or terminate treatment in conjunction with individual patient response.

For any immunosuppressive agent and other active agents used in the methods of the present invention, a therapeutically effective dose for humans can be estimated initially from non-human animal models.

Toxicity and therapeutic efficacy of the compounds described herein can be determined by standard pharmaceutical procedures in experimental animals, e.g., by determining the $LD_{50}$, (the dose lethal to 50% of the population tested) and the $ED_{50}$ (the dose therapeutically effective in 50% of the population tested). The dose ratio between toxic and therapeutic effect is the therapeutic index and can be expressed as the ratio between $LD_{50}$ and $ED_{50}$. Compounds which exhibit high therapeutic indices are preferred. The data obtained from these nonhuman animal studies can be used in formulating a dosage range that is not toxic for use in humans. The dosage of such compounds lies preferably within a range of circulating concentrations that include the $ED_{50}$ with little or no toxicity. The exact formulation, route of administration and dosage can be chosen by the individual physician in view of the patient's condition. (See, e.g., Fingl et al. (1975) In: *The Pharmacological Basis of Therapeutics,* Ch. 1).

A. Combination Therapy With Additional Active Agents

The therapeutic agents described above can be used alone or in combinations with each other (see, e.g., Aldrich, M., *Sleep Medicine,* Oxford University Press, New York, N.Y. U.S.A. 1999 and Robinson, A. and Guilleminault, C. "Narcolepsy," in *Sleep Disorders Medicine: Basic Science, Technical Considerations, and Clinical Aspects,* Chokroverty, S. (ed.) (Butterworh Heinemann Boston, Mass. U.S.A. 1999), pp 427–440; these references and the references cited therein are herein incorporated by reference). Combination therapy includes administration of a single pharmaceutical dosage formulation which contains an immunosuppressive agent and one or more additional active agents, as well as administration of an immunosuppressive agent and each active agent in its own separate pharmaceutical dosage formulation. For example, a glucocorticoid (e.g., dexamethasone, methylprednisolone, prednisolone, or prednisone) and azathioprine can be administered to the human subject together in a single oral dosage composition, such as a tablet or capsule, or each agent can be administered in separate oral dosage formulations. Where separate dosage formulations are used, an immunosuppressive agent and one or more additional active agents can be administered at essentially the same time (i.e., concurrently), or at separately staggered times (i.e., sequentially). Combination therapy includes all these regimens.

There can be many advantages to combining two therapeutic agents into one regime. For example, if one combines prednisone and azathioprine, prednisone acts within hours or days whereas aziathioprine can take up to a year bring about an effect. In addition, different therapeutic agents can suppress immune function in different ways which can be necessary for the overall desired immunosuppressive effects. The addition of one treatment agent to another effective regime can also significantly increase the effectiveness of the treatment regime.

An example of combination therapy that can be administered to a mammal susceptible to or suffering from narcolepsy to prevent, reduce, arrest, or reverse the development of narcoleptic symptoms comprises administering at least two of the following immunosuppressive agents: an NSAID, a glucocorticoid, hydroxychloroquine, sulfaxalazine, methotrexate, aurothioglucose, aurothiomalate, auronofin, D-penicillamine, azathioprine, cyclophosphamide, cyclosporin A, FK506, or rapamycin.

Another example of combination therapy is treating narcolepsy in a mammal susceptible to or suffering from narcolepsy with a therapeutically effective amount of a glucocorticoid compound used in combination with, for example, a non-steroidal anti-inflammatory compound, hydroxychloroquine, sulfaxalazine, methotrexate, aurothioglucose, aurothiomalate, auronofin, D-penicillamine, azathioprine, cyclophosphamide, cyclosporin A, FK506, or rapamycin. The immunosuppressive agents can also be effectively used in combination with, for example, antibodies to a cytokine or cytokine receptor, an anti-TNF-∀ antibody, a COX-1 inhibitor, a COX-2 inhibitor, an iNOS inhibitor, and an antioxidant.

Another regime combines an immunosuppressive agent with at least one of the following active agents: a CNS stimulant and/or an anticataplectic compound (e.g., caffeine, theophiline, theobromine, amphetamine, methylphenidate, dextroamphetamine, methamphetamine, pemoline, mazindol, modafinil, selegiline, ritanserin, viloxazine, CRL 40476, clomipramine, protriptyline, imipramine, desipramine, fluoxetine, paroxitine, sertraline, gammahydroxybutyrate (GHB), clonazepam, carbamazepine, or yohimbine). Other central nervous system stimulants or anticataplectic compounds can include tricyclic or tetracyclic antidepressants, selective serotonin reuptake inhibitors (SSRI) and monoamine oxidase (MAOs) inhibitors.

B. Pharmaceutical Compositions and Methods of Administration

The immunosuppressive agents and other active agents can be delivered or administered to a mammal, e.g., a human patient or subject, alone, in the form of a pharmaceutically acceptable salt or hydrolyzable precursor thereof, or in the form of a pharmaceutical composition wherein the compound is mixed with suitable carriers or excipient(s) in a therapeutically effective amount. A therapeutically effective regime means that a drug or combination of drugs is administered in sufficient amount and frequency and by an appropriate route to at least detectably prevent, delay, inhibit or reverse development of at least one symptom or biochemical maker of narcolepsy. A "therapeutically effective amount", "pharmacologically acceptable dose", "pharmacologically acceptable amount" means that a sufficient amount of an immunosuppressive agent or combination of agents is present to achieve a desired result, e.g., preventing, delaying, inhibiting or reversing a symptom or biochemical markers of narcolepsy and/or cataplexy or the progression of narcolepsy and/or cataplexy when administered in an appropriate regime.

The immunosuppressive agents and other active agents that are used in the methods of the present invention can be administered as pharmaceutical compositions comprising the immunosuppressive agent, together with a variety of other pharmaceutically acceptable components. Pharmaceutical compositions can be in the form of solids (such as powders, granules, dragees, tablets or pills), semi-solids (such as gels, slurries, or ointments), liquids, or gases (such as aerosols or inhalants).

Suitable formulations for use in the present invention are found in *Remington's Pharmaceutical Sciences* (Mack Publishing Company (1985) Philadelphia, Pa., $17^{th}$ edition) and Langer, *Science* (1990) 249:1527–1533, which are incorporated herein by reference. The pharmaceutical compositions described herein can be manufactured in a conventional manner, ie., mixing, dissolving, granulating, dragee-making, levigating, emulsifying, encapsulating, entrapping or lyophilizing processes.

In preparing the formulations of the present invention, pharmaceutically recognized equivalents of each of the compounds can be alternatively used. These pharmaceutically recognized equivalents can be pharmaceutically acceptable salts or pharmaceutically acceptable acid addition salts.

A pharmaceutically acceptable salt is a non-toxic alkali metal, alkaline earth metal, or an ammonium salt commonly used in the pharmaceutical industry including a sodium, potassium, lithium, calcium, magnesium, barium, ammonium, and protamine zinc salt, which is prepared by methods well known in the art. The term also includes a non-toxic acid addition salt, which is generally prepared by reacting the compounds of the present invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt which retains the biological effectiveness and properties of the free bases and which is not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like (see, e.g., Bundgaard, H., ed., *Design of Prodrugs* (Elsevier Science Publishers, Amsterdam 1985)).

The immunosuppressive agents and other active agents can be formulated with common excipients, diluents or carriers, and compressed into tablets, or formulated as elixirs or solutions for convenient oral administration. The immunosuppressive agents and other active agents can be can also be formulated as sustained release dosage forms and the like.

Administration of the compounds can be achieved in various ways, including oral, buccal, rectal, parenteral, intraperitoneal, intradermal, transdermal, intratracheal, and intramuscular administration. Moreover, the compound can be administered in a local rather than systemic manner, in a depot or sustained release formulation. In addition, the compounds can be admiinistered in a liposome.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, for injection, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the immunosuppressive agents and other active agents can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in a conventional manner.

For administration by inhalation, the compounds for use according to the present invention are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oil-based or aqueous vehicles, and can contain formulator agents such as suspending, stabilizing and/or dispersing agents. The compositions are formulated as sterile, substantially isotonic and in full compliance with all Good Manufacturing Practice (GMP) regulations of the U.S. Food and Drug Administration.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The immunosuppressive agents and other active agents can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In some methods, long-circulating, i.e., stealth, liposomes can be employed. Such liposomes are generally described in Woodle, et al., U.S. Pat. No. 5,013,556, the teaching of which is hereby incorporated by reference. The compounds of the present invention can also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

Certain organic solvents such as dimethylsulfoxide (DMSO) also can be employed, although usually at the cost of greater toxicity. Additionally, the compounds can be delivered using a sustained-release system, such as semi-permeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The therapeutically effective amounts for the methods of the present invention can depend on the subject being treated, on the subject's weight, the subject's overall health, the severity of the affliction, the manner of administration and the judgment of the prescribing physician.

(7) Antibody Tests for Narcolepsy and/or Cataplexy

Autoantibodies diagnostic of narcolepsy and/or cataplexy and the autoantigens recognized by such autoantibodies can be identified by screening extracts from one or more non-diseased individuals with sera or antibodies from diseased individuals in comparison with control sera or antibodies from nondiseased individuals. Extracts are obtained from the CNS tissue, in particular from the amygdala, the hypothalamus, and basal forebrain, where the greatest amount of neurodegeneration has been observed. Extracts are screened with sera or purified antibodies by a standard immunological assay(s) such as immunoblotting and/or immunoprecipitation. Autoantigen(s) is(are) recognized by antibodies and/or sera from most diseased individuals and not by antibodies and/or sera from most control individuals. A band from an immunoblot that is recognized by sera and/or antibodies from diseased individuals can be excised from a gel and subjected to amino acid sequencing or other characterization. If the autoantigen is a known protein or modified protein, a short peptide sequence (e.g., about six contiguous amino acids) is sufficient to identify the modified protein. If the autoantigen is a hitherto unknown (modified) protein, then amino acid sequence data can be used to generate DNA probes for use in screening a cDNA library to find the sequence for the autoantigen. Alternatively, a cDNA expression library can be screened using antibodies and/or sera from diseased individuals to find the sequence encoding the autoantigen. Once identified the autoantigen, portions thereof, and molecular analogs thereof can be used as diagnostic reagents for detection of autoantibodies in the diagnostic methods described above. Known proteins that are candidates for the autoantigen include the hypocretin (orexin) receptor 2 (Hcrtr2), the hypocretin (orexin) receptor 1 (Hcrtr1), hypocretin 1 (Hcrt1), and hypocretin 2 (Hcrt2).

T cells that recognize narcolepsy- and/or isolated cataplexy-related epitopes can be identified by in vitro assays that measure antigen-dependent proliferation, as determined by $^3$H-thymidine incorporation by primed T cells in response to a narcolepsy-related and/or isolated cataplexy-related epitopes (Burke et al., *J. Inf. Dis.* (1994) 170:1110–19), by antigen-dependent killing (cytotoxic T lymphocyte assay, Tigges et al., *J. Immunol.* 156:3901–3910), or by cytokine secretion. Alternatively in vitro proliferation assays in response to cytokines delivered without antigen can also be used.

(8) Kits

The invention further provides kits comprising an immunosuppressive agent which includes at least one of the following: a nonsteroidal anti-inflammatory, a glucocorticoid, hydroxychloroquine, sulfaxalazine, methotrexate, aurothioglucose, aurothiomalate, auronofin, D-penicillamine, azathioprine, cyclophosphamide, cyclosporin A, FK506, or rapamycin. Optional additional components of the kit include, for example, other active compounds, in combination with at least one of the following active agents such as, but not limited to, a CNS stimulant and/or an anticataplectic compound (e.g., caffeine, theophiline, theobromine, amphetamine, methylphenidate, dextroamphetamine, methamphetamine, pemoline, mazindol, modafinil, selegiline, ritanserin, viloxazine, CRL 40476, clomipramine, protriptyline, imipramine, desipramine, fluoxetine, paroxitine, sertraline, gammahydroxybutyrate (GHB), clonazepam, carbamazepine, or yohimbine). Other CNS stimulants or anticataplectic compounds can include tricyclic or tetracyclic antidepressants, SSRI and MAO inhibitors. Usually, the kit also contains instructions for carrying out the methods.

EXAMPLES

Example 1

The University of California, Los Angeles, maintains a colony of genetically narcoleptic/cataplectic Doberman pinschers which transmit the disorder in an autosomal recessive fashion. A litter of six narcoleptic dogs were used in this experiment. Two males and one female were immunosuppressed and the other three littermates (two females and one male) were used as controls. The dogs were immunosuppressed beginning exactly at three weeks of age. Three immunosuppressive regimes were tried: 1) On one male, methylprednisolone 10/mg/kg/day orally (PO), azathioprine 2 mg/kg/day PO, and cyclosporin A 2.0 mg/kg/week PO; 2) On another male, methylprednisolone 10/mg/kg/day PO, azathioprine 2 mg/kg/day PO, and methotrexate 0.4 mg/kg/week PO; and 3) On the female, methylprednisolone 10/mg/kg/day PO, and azathioprine 2 mg/kg/day PO.

The doses were administered to treated animals by nasogastric (NG) tubes; the diluted volumes of these administered drugs ranged from three to eight milliliters, in one dose dissolved and/or suspended, depending on the medication, in purified water. Control dogs received the same volumes of water through NG tubes. The dogs were fully weaned by six weeks. After two months of age, the treated dogs were administered all medications PO in balls of canned food while control dogs were given balls of canned food not containing any medication.

Throughout the study blood counts, liver function and thyroid function were monitored. Occasionally, ten to twenty times, treatment medications were reduced or eliminated temporarily, to alleviate indications of impending severe liver damage, and general infection, such as septicemia or gastrointestinal (GI) tract infections. Treatments for any problems were carried out under veterinary supervision.

In human adolescents and adults, it would be unusual to see any dangerous side effects with most of the drugs of our immunosuppressive regime, if the drugs were given at or under FDA approved limits.

The effects of our immunosuppressive regime were measured by three methods: the food elicited cataplexy test (FECT), the modified food elicited cataplexy test (mFECT), and actigraphy. Both the FECT and mFECT are methods of quantifying cataplexy in a narcoleptic dog, whereas actigraphy measures sleep and waking patterns.

The FECT test was used to monitor the dogs until they were seven months old. After seven months of age, the mFECT test was used. The particular FECT test that was used to monitor the dogs in this study involves recording the time the dogs spend eating eight balls of ⅜ cup of food spaced at five inch intervals. Cataplexies caused by the excitement of eating and the necessity of movement to reach the next food pile prevent food ingestion and lengthen the FECT time. However, with daily testing, the animals are able to learn to improve their test performance, even while their overall symptoms are constant or worsening. This results in a lowered FECT score even in an intensely symptomatic animal and decreased differences in FECT times between animals with obvious differences in symptomatology. Therefore the mFECT was developed.

The mFECT observes the animal eating a fixed amount of its usual food during its normal daily feeding from its bowl. Since the animal is fed this way every day and there is no locomotion required, there is no practice effect. Cataplexy duration, as well as the duration of eating the entire amount of food, not confounded by locomotor learning, can be observed. The mFECT tests were conducted by a technician blind to the treatment conditions of the animals.

The protocol for the mFECT is as follows: 1) 30 gm/kg of Eukanuba™ formula dog food are soaked in 30 cc/kg of water for 15 minutes. The food is presented to the dog in its usual metal bowl between 8:00 and 10:00 am each day. The dog is observed for 10 minutes or until the food is finished, whichever is shorter, starting with the introduction of the food bowl; 2) Cataplexy time is scored when any of the following criteria are present: falling, collapse of the fore- or hindlimbs, sagging posture with minimized movements and/or swaying, interruption or slowing of eating caused by jaw hypotonia, drooping eyelids, or sudden or lengthy hypotonia of the tail uncharacteristic for the dog; 3) Total time spent eating is also scored.

Figure 1:
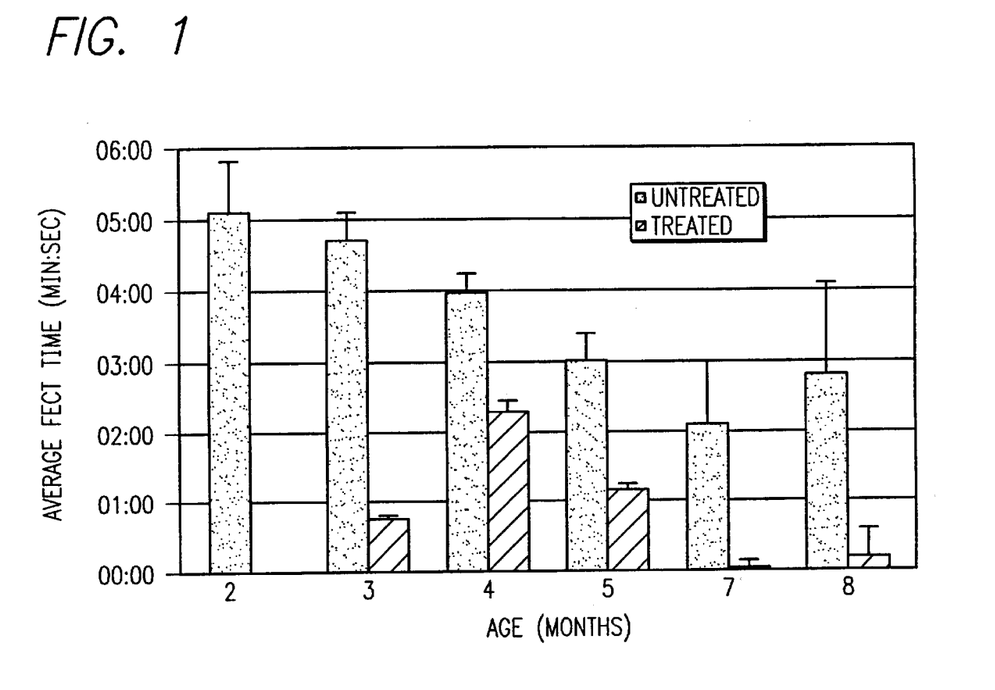
FIG. 1. Effect of immunosuppressive agents on the development of cataplexy in a narcoleptic canine model.
Figure 2A:
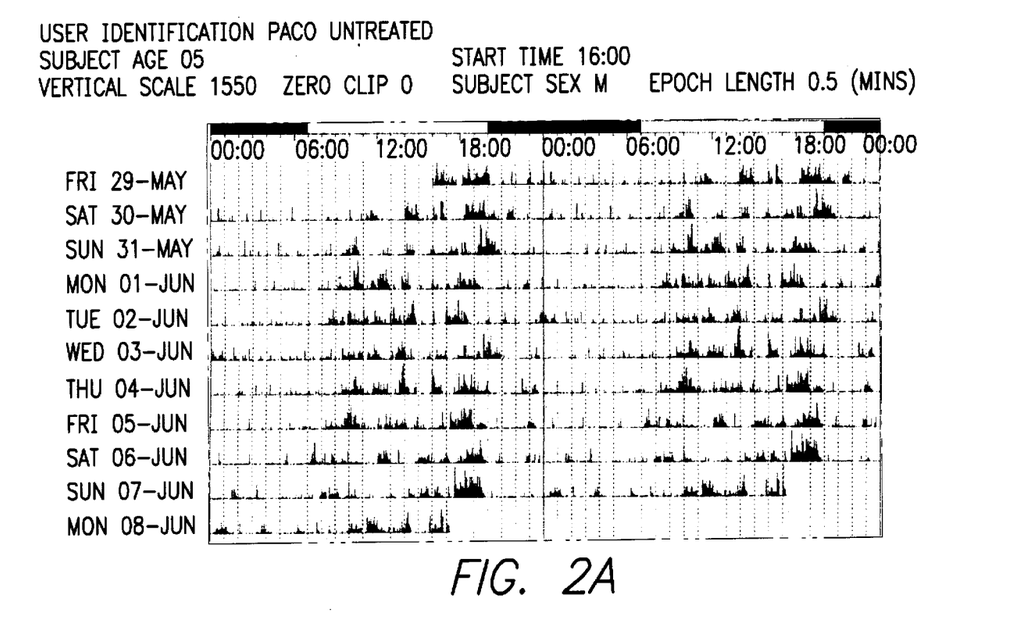
Figure 2B:
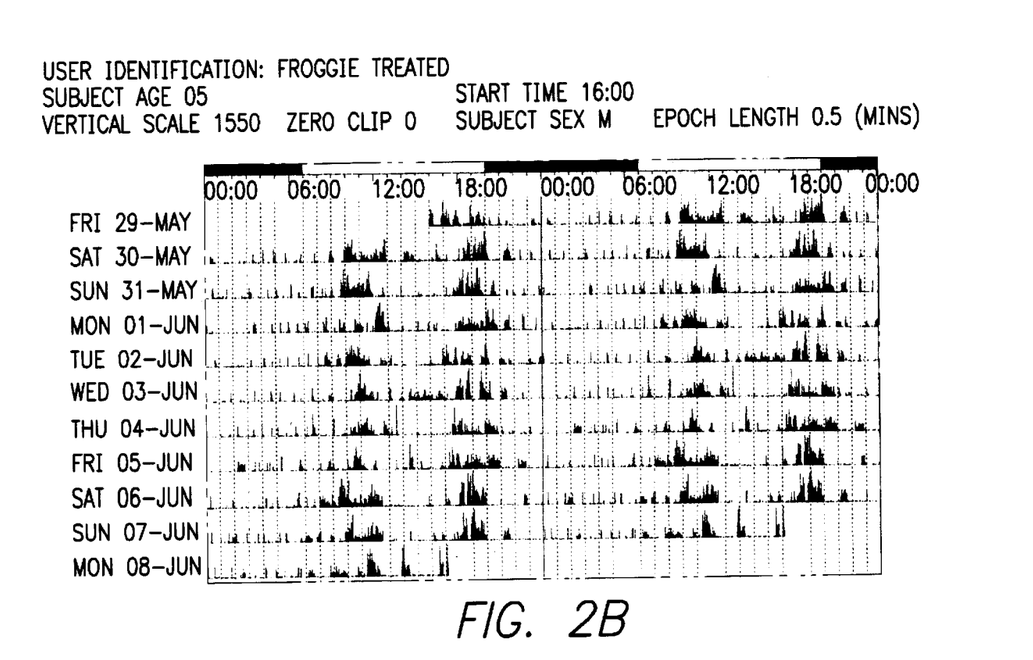
Figure 2C:
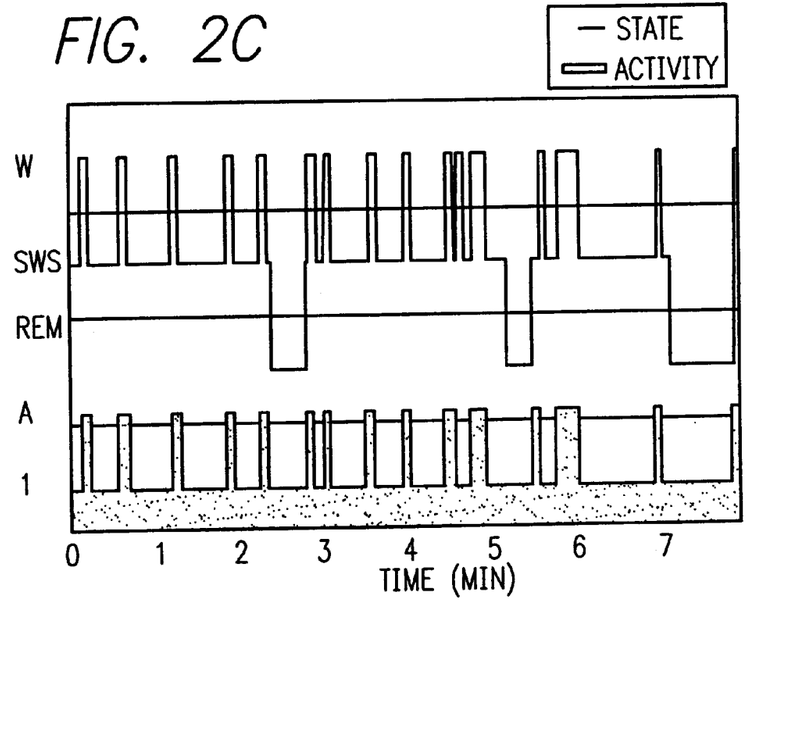
Figure 2D:
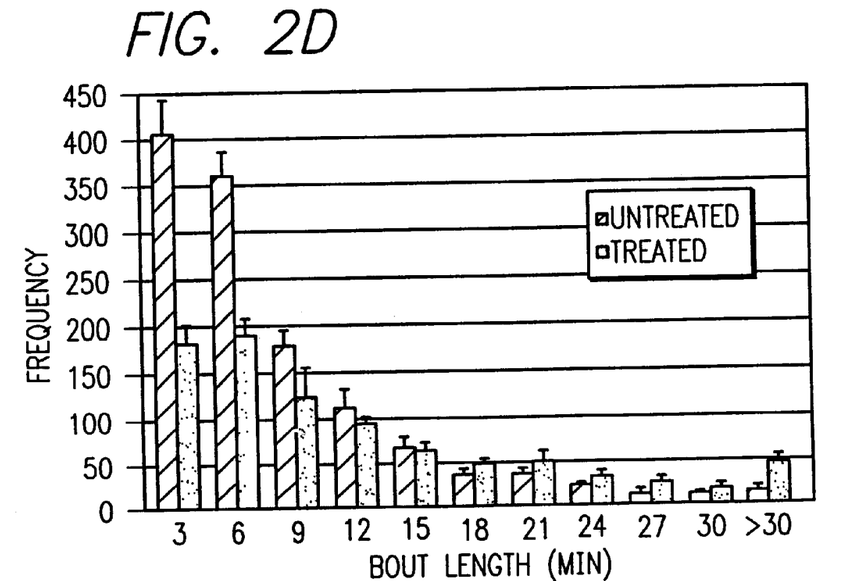

Treated animals did not have any cataplexy until three months of age. All untreated dogs had cataplexy by two months of age. Azathioprine and methotrexate treatment were terminated at approximately six months of age, and methylprednisolone dosages were tapered (to both eliminate potential liver toxicity and bring the animals off the treatment regime). Treatment produced a significant ($p<0.0001$, $F=27.8$, 1&24 df) and long lasting reduction of cataplexy, as measured by the FECT and the mFECT. (See FIG. 1.). In addition, the treated animals subjectively appeared to experience substantially less cataplexy than the untreated animals.

Example 2

To confirm our initial findings we repeated our study in two additional litters comprising a total of 6 dogs, 4 in one litter and 2 in the second litter. Three of the dogs (three females) were subjected to the immunosuppression regimen similar to the one described above, except that methylprednisone dosages were started at 5 mg/kg/day, cyclosporine was eliminated, and methotrexate was reduced to 0.36 mg/kg/week and their littermates (two females and one male) served as controls. In these litters the immunosuppressive regime beginning 4 days after birth, rather than at 21 days as in the litter described above. We did this because our earlier work (Siegel, J. M., Nienhuis, R., Gulyani, S., Ouyang S., Wu, M. F., Mignot, E., Switzer, R. C. Comford, M. Neuronal degeneration in canine narcolepsy *J. Neuroscience* (1999) 19:48–257) had indicated that neurodegenerative processes in narcolepsy begin prior to one month of age. The dogs in the these two litters were 8 and 6 weeks old. The 8 week old litter consisted of 4 dogs. The two dogs in this litter that had not been given the immunosuppressive regime are fully symptomatic with repetitive and sustained cataplexy while eating. They were symptomatic for 5 weeks. The two immunosuppressed animals in this litter showed no signs of cataplexy or any other symptoms of narcolepsy. They are active and alert. Similarly, in the second litter, the control dog has shown episodes of cataplexy for the past 3 weeks. The immunosuppressed animal has shown no signs of cataplexy. These animals are continuing to be monitored, it is expected, and based on the results so far, that the treated animals will have an even greater diminution of symptoms than the litter described above. It is possible that they may be completely spared the symptoms of narcolepsy.

Example 3

Figure 3A:
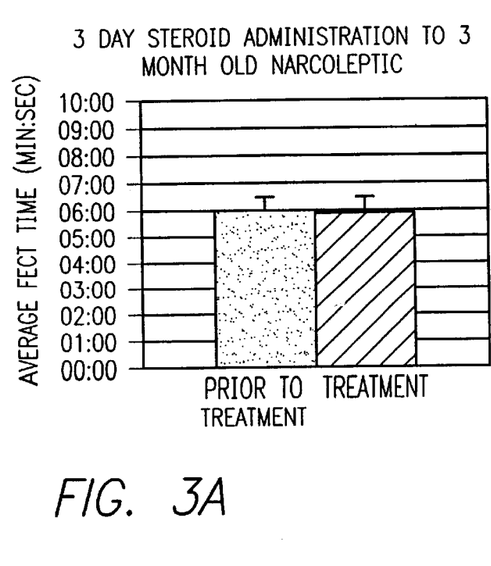
Figure 3B:
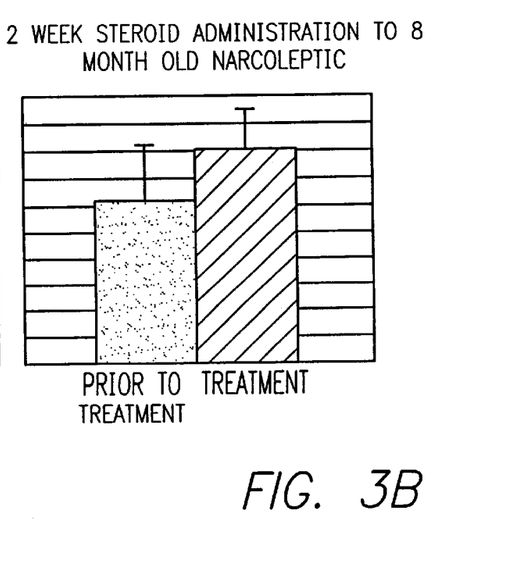

To confirm that the relief provided by the immunosuppressive regimes in the first example was not confined to a transient reduction in symptoms only experienced with concurrent drug adminstration, the following experiment was performed. A three month old control narcoleptic dog was treated for three days with the highest dosages given at that time to any of the treated dogs: methylprednisolone 5.1 mg/kg/day PO, azathioprine 2.0 mg/kg/day PO, and one dose of methotrexate 0.3 mg/kg PO. We also treated the same dog at eight months of age for two weeks with methylprednisolone 2.0 mg/day PO. In contrast to chronic immunosuppression, transient immunosuppression did not reduce symptoms (See FIG. 3.) This indicates that the systemic presence of the drugs did not have a direct effect on symptoms. Rather, the sustained drug treatment at levels to produce chronic immunosuppression prevented symptom development.

Actigraphs were then used to compare sleeping and waking patterns in the treated vs. untreated dogs. A methylprednisolone and methotrexate treated, and an untreated littermate each wore actigraphs during the same ten day period at five months of age. The actigraphs were inserted in collars of these two littermates starting at one month of age. The actigraphs sensed head motion (acceleration). Brain wave recordings in other genetically narcoleptic dogs of the same breed showed that periods of extended head immobility were sleep. Therefore, the actigraphic records allow us to distinguish sleep and waking and determine the duration of each period.

MiniMitter actigraphs with a 30 second epoch length were used. This allowed continuous recording period of activity and inactivity. The data were downloaded by placing the actigraphs on an inductively coupled actigraph reader. This downloaded data was plotted immediately as continuous graphs of the activity levels of each dog. Software further assisted with data analysis by calculating the duration of inactive periods, the distribution of periods of inactivity across the 24 hour cycle, and the mean amounts of activity during both day and night.

Actigraph data showed normalization of sleep with treatment in a narcoleptic dog (see FIG. 2). A and B show the double plotted actigraph data. The mean activity level for the treated dog was 8% higher than in the untreated dog. C shows the correlation between actigraphic discrimination of waking and polygraphically scored sleep in an adult narcoleptic dog implanted with brain wave (EEG) and electromyogram recording electrodes as described previously (Wu et al., 1999). Period of non-zero activity, as detected by actigraphy, corresponding to waking as scored by polygraphic measures. W, waking; SWS, slow wave sleep; REM, REM sleep. A, active; I, inactive, determined by simultaneous actigraph recording. D shows the nighttime sleep cycle duration as detected by actigraphy. Untreated animals have significantly ($p<0.0001$, $F=11.6$, 4&12 df) more short sleep period lengths and fewer long sleep period lengths than treated littermates. Interrupted sleep is a characteristic of human and canine narcoleptics. The changes with treatment represent a normalization of the narcoleptic sleep cycle.

Example 4

Figure 4A:
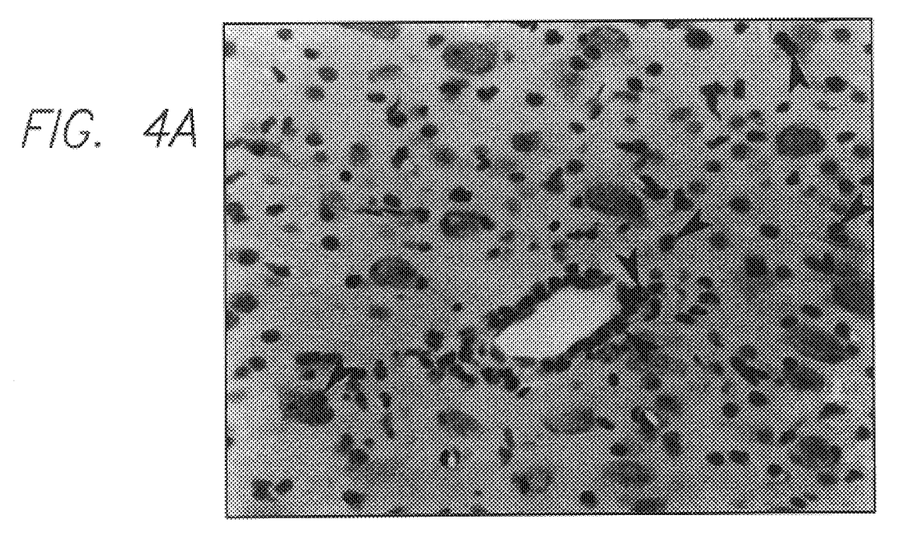
Figure 4B:
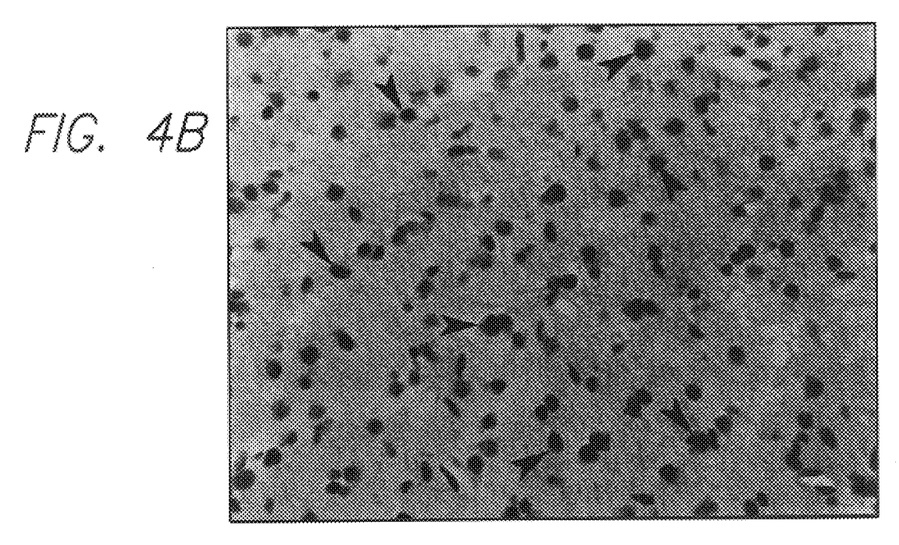

A study was conducted to determine the presence of $CD3^+$ T cells in the amygdala of a one month old narcoleptic dog (See FIGS. 4A and 4B; magnifications are at 300x.). The staining for $CD3^+$ T cells was accomplished by using rat anti-CD3 synthetic peptide (Serotec, Raleigh, N.C.), which is known to crossreact with canine CD3, using standard immunohistochemistry procedures. The amygdala is an area in which the greatest amount of neurodegeneration has been observed in previous work (Siegel, J., *J. Neurosci.* (1999) 19(1):248–257). In the gray matter region of the basolateral nucleus T cells (brown, DAB labeled; top) are visible adjacent to a neuronal soma (left), around a blood vessel and in the parenchyma. The bottom photo shows a much higher concentration of T cells in a white matter region; only a few cells have been labeled with arrows. In an age and breed matched control brain, few or no $CD3^+$ cells were seen in the same region. $CD3^+$ T cells are therefore present in at least some sites of neurodegeneration in the narcoleptic canine brain.

These examples and experiments have shown that 1) the immunosuppressive regime permanently reduces the symptoms of cataplexy in the narcoleptic Doberman pinscher; 2) the effect of the immunosuppressive regime used did not directly affect symptoms in these dogs, but rather worked through long-term effects of the immunosuppressive regime; 3) the immunosuppressive regime normalized the narcoleptic sleep cycle in these genetically narcoleptic Doberman pinschers; and 4) CD3$^+$ T cells are present in at least some areas of known neurodegeneration in the narcoleptic Doberman pinscher, but not in corresponding areas of a normal control Doberman pinscher.

Although the foregoing invention has been described in detail for purposes of clarity of understanding, it can be obvious that certain modifications can be practiced within the scope of the appended claims. All publications and patent documents cited above are hereby incorporated by reference in their entirety for all purposes to the same extent as if each were so individually denoted.

What is claimed is:

1. A method of treating narcolepsy or isolated cataplexy in a patient, comprising:administering to a patient susceptible to or suffering from narcolepsy a therapeutically effective regime of an immunosuppressive agent.

2. The method of claim 1, wherein the patient is free of diseases other than narcolepsy or isolated cataplexy requiring immunosuppressive treatment.

3. The method of claim 1, wherein the therapeutically effective regime is administered responsive to diagnosis of narcolepsy or isolated cataplexy or a biochemical or genetic marker thereof.

4. The method of claim 3, wherein the administration ameliorates a symptom of narcolepsy or isolated cataplexy within six months of treatment.

5. The method of claim 1, wherein the immunosuppressive agent is at least one agent selected from the group consisting of a nonsteroidal anti-inflammatory, a glucocorticoid, hydroxychloroquine, sulfaxalazine, methotrexate, aurothioglucose, aurothiomalate, auronofin, D-penicillamine, azathioprine, cyclophosphamide, cyclosporin A, FK506, and rapamycin.

6. The method of claim 1, wherein at least two immunsuppressive agents are administered, the two agents being selected from the group consisting of a nonsteroidal anti-inflammatory, a glucocorticoid, hydroxychloroquine, sulfaxalazine, methotrexate, aurothioglucose, aurothiomalate, auronofin, D-penicillamine, azathioprine, cyclophosphamide, cyclosporin A, FK506, and rapamycin.

7. The method of claim 1, wherein the immunosuppressive agent is administered in combination with at least one agent selected from the group consisting of a tricyclic antidepressant, a tetracyclic antidepressant, a selective serotonin reuptake inhibitor (SSRI), a monoamine oxidase (MAO) inhibitor, caffeine, theophiline, theobromine, amphetamine, methylphenidate, dextroamphetamine, methamphetamine, pemoline, mazindol, modafinil, selegiline, ritanserin, viloxazine, CRL 40476, clomipramine, protriptyline, imipramine, desipramine, fluoxetine, paroxitine, sertraline, gammahydroxybutyrate (GHB), clonazepam, carbamazepine, and yohimbine.

8. The method of claim 1, wherein the immunosuppressive agent is a glucocorticoid compound.

9. The method of claim 8, wherein the glucocorticoid compound is dexamethasone, methylprednisolone, prednisolone, or prednisone.

10. The method of claim 8, wherein the glucocorticoid compound is administered in combination with a therapeutically effective amount of a nonsteroidal anti-inflammatory agent.

11. The method of claim 10, wherein the nonsteroidal anti-inflammatory agent is an aspirin compound (acetylsalicylate), a non-aspirin salicylate, diclofenac, diflunisal, etodolac, fenoprofen, flurbiprofen, ibuprofen, indomethacin, ketoprofen, meclofenamate, naproxen, naproxen sodium, phenylbutazone, sulindac, or tometin.

12. The method of claim 8, wherein the glucocorticoid compound is administered in combination with a therapeutically effective amount of an agent selected from the group consisting of hydroxychloroquine, sulfaxalazine, methotrexate, aurothioglucose, aurothiomalate, auronofin, D-penicillamine, azathioprine, cyclophosphamide, cyclosporin A, FK506, and rapamycin.

13. The method of claim 1, wherein the patient is human.

14. The method of claim 1, wherein the immunosuppressive agent is administered by intravenous infusion, transdermal delivery, intramuscular delivery, subcutaneous delivery, intracerebralventricular delivery, inhalation, or oral delivery.

15. The method of claim 1, wherein the regime is administered from birth of the patient to prevent or delay onset of narcolepsy or isolated cataplexy in the patient.

16. The method of claim 1, wherein the therapeutically effective regime is administered after diagnosis of a symptom of narcolepsy or isolated cataplexy in the patient to relieve the symptom, or arrest or inhibit further development of the symptom.

17. The method of claim 1, wherein the immunosuppressive agent is administered together with a pharmaceutically acceptable carrier as a pharmaceutical composition.

18. The method of claim 1, wherein the patient shows HLA-DQB1*0602-linked sleepiness and the treatment inhibits, arrests or reverses the HLA-DQB1*0602-linked sleepiness.

19. The method of claim 1, wherein the patient shows neurodegeneration and the treatment inhibits, arrests or reverses the neurodegeneration.

20. The method of claim 1, wherein the immunosuppressive agent inhibits T cell, B cell, or monocyte infiltration associated with narcolepsy or isolated cataplexy in the patient.

21. The method of claim 1, wherein the immunosuppressive agent prevents or reduces the occurrence of one or more symptoms associated with narcolepsy or isolated cataplexy in the patient.

22. The method of claim 21, wherein the prevention or occurrence of one or more symptoms is detected within six months of administering treatment.

23. The method of claim 21, wherein the immunosuppressive agent prevents or reduces at least one symptom selected from the group consisting of abnormal sleep features, overwhelming episodes of sleep, excessive daytime somnolence, abnormal REM sleep, hypnagogic and hypnopompic hallucinations, disturbed nocturnal sleep, cataplexy, and sleep paralysis.

24. The method of claim 1, wherein the immunosuppressive agent is administered before onset of symptoms of narcolepsy or isolated cataplexy in a patient.

25. The method of claim 1, wherein the patient is a human having a risk factor indicating susceptibility to narcolepsy or isolated cataplexy.

26. The method of claim 25, further comprising detecting a genetic marker in the human associated with susceptibility to narcolepsy or isolated cataplexy.

27. The method of claim 26, wherein the genetic marker is HLA-DQB1*0602.

28. The method of claim 25, wherein the risk factor is a mutation or deletion in any Hypocretin (Orexin) Receptor gene.

29. The method of claim 25, wherein the risk factor is a mutation or deletion in the Hypocretin (Orexin) gene.

30. The method of claim 25, wherein the risk factor is a mutation or deletion in the Hypocretin (Orexin) Receptor 2 gene.

31. The method of claim 1, further comprising monitoring the patient to assess the effects of treatment.

32. The method of claim 31, wherein the monitoring comprises conducting a nocturnal polysomnogram (PSG), Multiple Sleep Latency Test (MSLT), Epworth Sleepiness Scale (EPS) questionnaire, Maintenance of Wakefulness Test (MWT), pupilography, electroencephalograms, or electroencephalographic spectral analysis, actigraphy, or maintaining a log of incidence of cataplexy including their number, severity and duration.

33. The method of claim 31, wherein the monitoring comprises conducting immune or histological assays to determine the presence or absence of neurodegeneration, nerve cell death, T cell infiltration, B cell infiltration, monocytic infiltration, apoptosis, or necrosis.

\* \* \* \* \*